United States Patent [19]
de Ruggieri et al.

[11] 4,048,159
[45] Sept. 13, 1977

[54] TETRAHYDROPYRANYL ETHERS OF ESTROGENS

[75] Inventors: Pietro de Ruggieri; Orazio Sighinolfi, both of Milan, Italy

[73] Assignee: Farmila Farmaceutici, Italy

[21] Appl. No.: 633,477

[22] Filed: Nov. 19, 1975

[30] Foreign Application Priority Data

Dec. 13, 1974  Italy ................................ 30574/74

[51] Int. Cl.$^2$ ............................................. C07J 17/00
[52] U.S. Cl. ........................ 260/239.55 R; 260/397.5
[58] Field of Search ....................... 260/239.55, 397.5;
Machine Searched Steroids

[56] References Cited

U.S. PATENT DOCUMENTS

| 3,470,159 | 9/1969 | Marshall | 260/239.55 |
| 3,481,924 | 12/1969 | de Ruggeri et al. | 260/239.55 |

*Primary Examiner*—Elbert L. Roberts
*Attorney, Agent, or Firm*—Hill, Gross, Simpson, Van Santen, Steadman, Chiara & Simpson

[57] ABSTRACT

Tetrahydropyranyl ethers of estrogens have interesting properties in the cure of climateric and menopausal disturbances, with an excellent dissociation index between their selective effect on the vagina and their very small or zero effect on the endometrium.

14 Claims, No Drawings

TETRAHYDROPYRANYL ETHERS OF ESTROGENS

This invention provides, as new compounds, the estrogen derivatives of the formula:

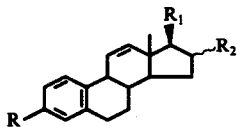

where R is hydroxy, lower alkoxy, 2'-tetrahydropyranyloxy or benzyloxy, $R_1$ is β-2'-tetrahydropyranyloxy, $R_2$ is keto, α-hydroxy, β-hydroxy, α-2'-tetrahydropyranyloxy, β-2'-tetrahydropyranyloxy.

It should be noted that the introduction of the tetrahydropyranyloxy radical comprising one asymmetrical carbon atom leads to two diasteroisomers R and S The present invention therefore relates both to the mixture R + S and to the two separate R and S diastereoisomers.

These compounds have favorable therapeutic properties in the cure of climateric and menopausal disturbances, with an excellent dissociation index between their selective effect on the vagina and their very small or zero effect on the endometrium; the administration of the compounds can be effected orally, in the form of capsule, tablets, dragees or by injection in oil solution, with daily dosages from 1 to 25 mg. for treatments continued for 3 weeks, followed by an interruption of 1 week, or for more extended cycles.

The starting materials, 3-methoxy-estra-1,3,5(10)-trien-17β-ol-16-one (Ia) and the 3-benzyloxy-derivative analogue (Ib), may be prepared in accordance with the method of M. N. Huffman, J. Biol. Chem. 169, 167 (1974) and J. Biol. Chem. 172, 325 (1948).

The subsequent processing to obtain certain key intermediates is shown in equation 1:

EQUATION 1

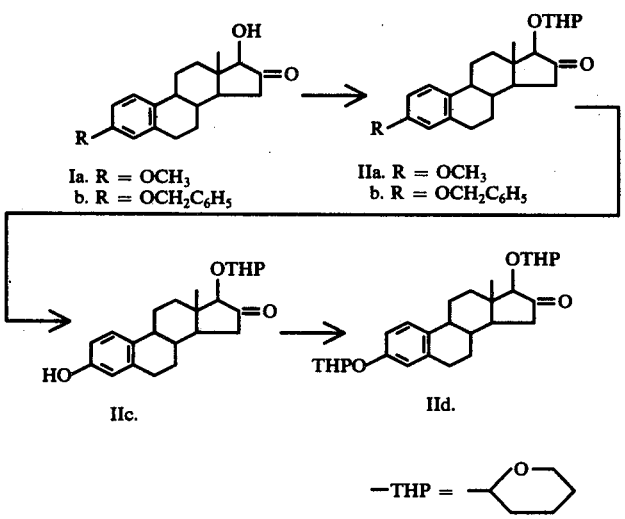

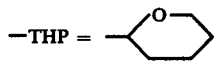

with a possible α and β anomer configuration, the α (axial) configuration being the preferred, as it is stabilised by two ethereal dipoles of antiparallel position on the two oxygen atoms present.

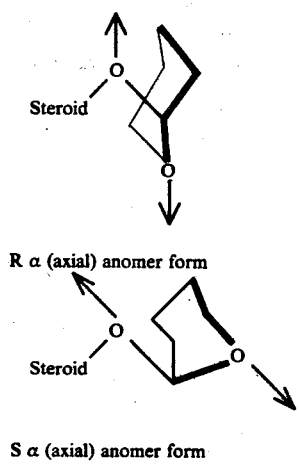

Compounds (Ia) and (Ib) when reacted with 2,3-dihydropyran, either ure or diluted with a suitable solvent and in the presence of an acid catalyst, preferably p-toluenesulphonic acid or phosphorus oxychloride, gave 3-methoxy-17β-(2'-tetrahydropyranyloxy)-estra-1,3,5(10)-trien-16-one (IIa) and the 3-benzyloxy-derivative analogue (IIb) respectively.

This latter (IIb), when subjected to destructive hydrogenation in the presence of a catayst (i.e., debenzylating by catalytic hydrogenation) such as 10% Pd on carbon in a solvent such as pure ethanol or ethanol mixed with dioxane or ethyl acetate, gave 17β-(2'-tetrahydropyranyloxy)-estra-1,3,5(10)-trien-3-ol-16-one (IIc), from which the corresponding phenolic ether 3,17β-bis-(2'-tetrahydropyranyloxy)-estra-1,3,5(10)-trien-16-one (IId) was obtained by further reaction with 2,3-dihydropyran.

Equation 2 shows the successive transformations carried out on the three 17β-(2'-tetrahydropyranyloxy)-16-ones (IIa) (IIb) and (IId) previously obtained.

EQUATION 2

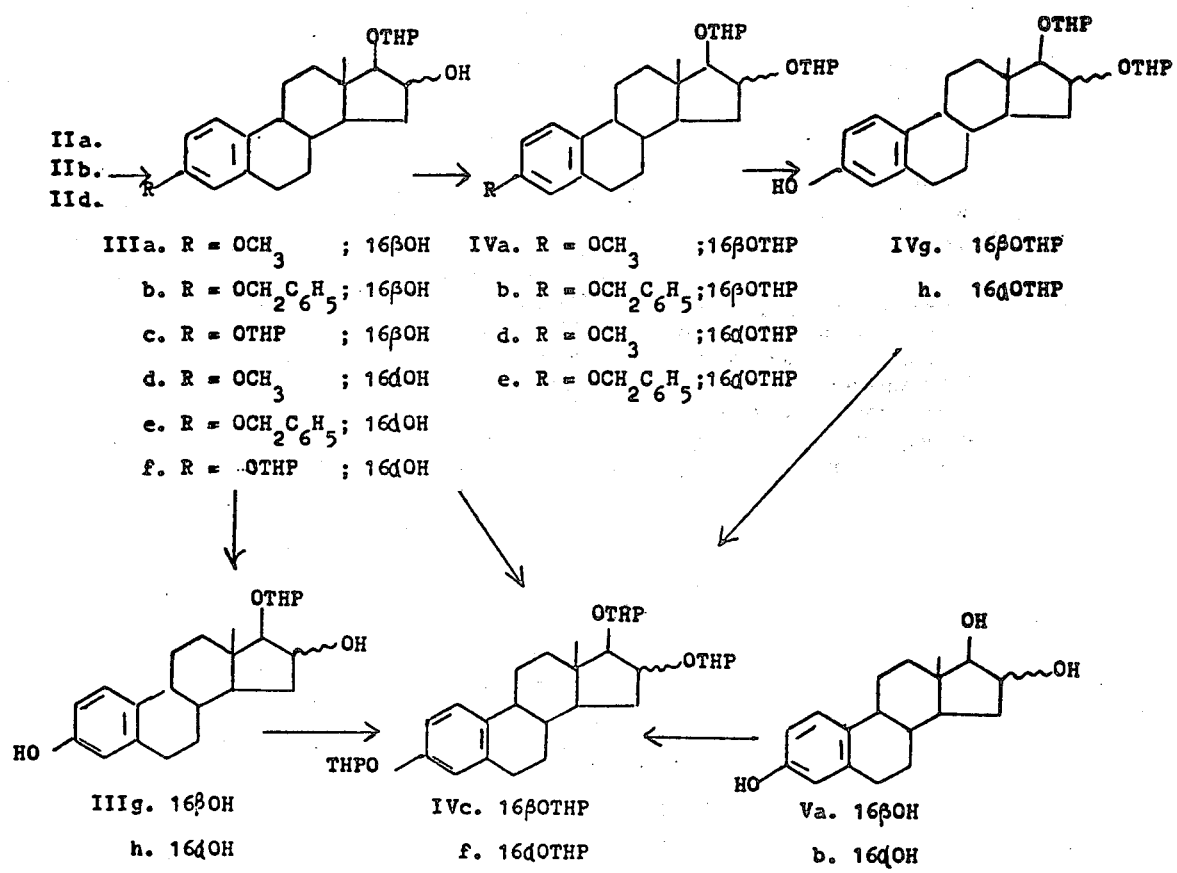

IIIa. R = OCH$_3$ ; 16βOH  
b. R = OCH$_2$C$_6$H$_5$ ; 16βOH  
c. R = OTHP ; 16βOH  
d. R = OCH$_3$ ; 16αOH  
e. R = OCH$_2$C$_6$H$_5$ ; 16αOH  
f. R = OTHP ; 16αOH

IVa. R = OCH$_3$ ; 16βOTHP  
b. R = OCH$_2$C$_6$H$_5$ ; 16βOTHP  
d. R = OCH$_3$ ; 16αOTHP  
e. R = OCH$_2$C$_6$H$_5$ ; 16αOTHP

IVg. 16βOTHP  
h. 16αOTHP

IIIg. 16βOH  
h. 16αOH

IVc. 16βOTHP  
f. 16αOTHP

Va. 16βOH  
b. 16αOH

On stereospecific reduction of the ketone function with complex metal hydrides such as NaBH$_4$ in solvents such as pure ethanol or ethanol mixed with other solvents, or LiAlH$_4$ in ethyl ether or tetrahydrofuran, derivatives of the epiestriol series (16βOH) were obtained, namely 3-methoxy-17β-(2'-tetrahydropyranyloxy)-estra-1,3,5(10)-trien-16β-ol (IIIa), the 3-benzyloxy analogue (IIIb) and 3,17β-bis-(2'-tetrahydropyranyloxy)-estra-1,3,5(10)-trien-16β-ol (IIIc).

On treating compounds (IIIa) and (IIIb) with 2,3-dihydropyran, 3-methoxy-16β,17β-bis-(2'-tetrahydropyranyloxy)estra-1,3,5(10)-triene (IVa) and the 3-benzyl derivative analogue (IVb) were obtained respectively. 16β,17β-bis-(2'-tetrahydropyranyloxy)-estra-1,3,5(10)-trien-3-ol (IVg) is finally obtained from this by destructive hydrogenation of the benzyl ether group. The direct destructive hydrogenation carried out on the 3-benzyloxy-17β-(2'-tetrahydropyranyloxy)-estra-1,3,5(10)-trien-16β-ol (IIb) led instead to 17β-(2'-tetrahydropyranyloxy)-estra-1,3,5(10)-trien-3,16β-diol (IIIg), from which 3,16β,17β-tris-(2'-tetrahydropyranyloxy)-estra-1,3,5(10)-triene (IVc) was obtained by simultaneous etherification of the phenolic and alcoholic groups with 2,3-dihydropyran, and which can be obtained directly from the 16-epiestriol (Va), from (IVg) or from (IIIc) by etherification with 2,3-dihydropyran.

The derivatives of the estriol series (16αOH) indicated in equation 2 as (IVd), (IVe), (IVh), (IIIh) and (IVf) were obtained from the previous compounds (IIa), (IIb) and (IId), but carrying out the reduction with sodium metal in n-propanol at boiling point, and repeating the same series of reactions.

The following Examples illustrate the present invention.

EXAMPLE 1

3-Benzyloxy-17β-(2'-tetrahydropyranyloxy)-estra-1,3,5(10)-trien-16-one (IIb)

Five parts of 3-benzyloxy-estra-1,3,5(10)-trien-17β-ol-16-one (Ib) dissolved in 300 parts of anhydrous benzene are added to a solution of 5 parts of 2,3-dihydropyran and 0.15 parts of p-toluenesulphonic acid in 250 parts of anhydrous benzene. After leaving overnight at ambient temperature, the reaction mixture is washed first with an aqueous 10% NaHCO$_3$ solution and then with water until neutral. After drying, the organic phase is concentrated to dryness under vacuum. After crystallization from ethyl ether, the residue gives 4.3 parts of 3-benzyloxy-17β-(2'-tetrahydropyranyloxy)-estra-1,3,5(10)-trien-16-one (IIb).

The product has a m.p. of 164°–165° C. and $[\alpha]_D = -55°$ (chloroform).

EXAMPLE 2

3-Methoxy-17β-(2'-tetrahydropyranyloxy)-estra-1,3,5(10)-trien-16-one (IIa)

Using the same process as described in Example 1 and starting from 2 parts of 3-methoxy-estra-1,3,5(10)-trien-17β-(2'-tetrahydropyranyloxy)-estra-1,3,5(10)-trien-16-one (IIb) are obtained after crystallization from methanol.

The product has a m.p. of 120°–122° C. and $[\alpha]_D = -140°$ (chloroform).

EXAMPLE 3

17β-(2'-tetrahydropyranyloxy)-estra-1,3,5(10)-trien-3-ol 16-one (IIc)

1.5 parts of carbon containing 5% of palladium are added to a solution of 1.5 parts of 3-benzyloxy-17β-(2'- tetrahydropyranyloxy)-estra-1,3,5(10)-trien-16-one (IIb) in 50 parts of dioxane and 80 parts of ethanol. After this, the mixture is shaken and made to absorb hydrogen at ambient temperature and pressure until no more is absorbed. After removing the catalyst by filtration, the solvent is evaporated to dryness under vacuum. The residue is crystallized from methanol to give 0.9 part of 17β-(2'-tetrahydropyranyloxy)-estra-1,3,5(10)-trien-3-ol-16-one (IIc) which has a m.p. of 210°–212° C. and $[\alpha]_D = -34°$ (chloroform).

EXAMPLE 4

3,17β-bis-(2'-tetrahydropyranyloxy)-estra-1,3,5(10)-trien-16-one (IId)

A solution of 2.5 parts of 17β-(2'-tetrahydropyranyloxy)-estra-1,3,5(10)-trien-3-ol-16-one (IIc) in 40 parts of tetrahydrofuran mixed with 90 parts of anhydrous benzene is added to a solution of 5 parts of 2,3-dihydropyran in 180 parts of anhydrous benzene containing 0.15 part of p-toluenesulphonic acid. After leaving overnight at room temperature, it is washed with a 10% NaHCO₃ solution and then with water until neutral. The organic phase is dried and then concentrated to dryness under vacuum. The oily residue is eluted over an Al₂O₃ chromatograph column (activity II, according to Brockmann) with a hexane-ethyl ether mixture to give 2.2 parts of 3,17β-bis-(2'-tetrahydropyranyloxy)-estra-1,3,5(10)-trien-16-one (IId) of m.p. 117°–120° C. and $[\alpha]_D = -46°$ (chloroform).

EXAMPLE 5

3,17β-bis-(2'-tetrahydropyranyloxy)-estra-1,3,5(10)-trien-16β-ol (IIIc)

A solution of 0.6 parts of NaBH₄ in 5 parts of water is dripped into a boiling solution of 1 part of 3,17β-bis-(2'-tetrahydropyranyloxy)-estra-1,3,5(10)-trien-16-one (IId) in 70 parts of ethanol. After boiling for about half an hour, the mixture is cooled and then poured into water. The product is then extracted using a total of 85 parts of ethyl ether. The organic phase is washed with water and dried, and then concentrated to dryness under vacuum. The residue is crystallized from methanol to give 0.5 part of 3,17β-bis-(2'-tetrahydropyranyloxy)-estra-1,3,5(10)-trien-16β-ol (IIIc) of m.p. 115°–117° C. and $[\alpha]_D = +54.5°$ (chloroform).

EXAMPLE 6

3,17β-bis-(2'-tetrahydropyranyloxy)-estra-1,3,5(10)-trien-16α-ol (IIIf)

3 Parts of 3,17β-bis-(2'-tetrahydropyranyloxy)estra-1,3,5(10)-trien-16-one (IId) are dissolved in 65 parts of n-propanol. 1.8 Parts of finely divided sodium metal are added and the mixture is refluxed for about half an hour, after which time all the sodium has been consumed. After cooling, the mixture is poured into a large excess of ice-cold water and neutralised with a saturated solution of KH₂PO₄.

The crude product separated by filtration (2.4 parts) is impure, and is therefore chromatographed over Al₂O₃ (activity II, according to Brockmann), eluting with a hexane-ethyl ether mixture. The useful fractions are mixed together and then crystallised from ether to give 0.5 part of 3,17β-bis-(2'-tetrahydropyranyloxy)-estra-1,3,5(10)-trien-16α-ol (IIIf) of m.p. 132°–135° C. and $[\alpha]_D = +36.5°$ (chloroform).

EXAMPLE 7

3-Benzyloxy-17β-(2'-tetrahydropyranyloxy)-estra-1,3,5(10)-trien-16β-ol (IIIb)

Using a process very similar to that described under Example 5, but employing ethanol in mixture with dioxane as solvent and starting from 1.5 parts of 3-benzyloxy-17β-(2'-tetrahydropyranyloxy)-estra-1,3,5(10)-trien-16-one (IIb), crystallization from ethyl ether gives 1.2 parts of 3-benzyloxy-17β-(2'-tetrahydropyranyloxy)-estra-1,3,5(10)-trien-16β-ol (IIIb) of m.p. 130°–131° C. and $[\alpha]_D = +99°$ (chloroform).

EXAMPLE 8

3-Methoxy-17β-(2'-tetrahydropyranyloxy)-estra-1,3,5(10)-trien-16β-ol (IIIa).

Using a process identical with that described in Example 5 and starting from 1 part of 3-methoxy-17β-(2'-tetrahydropyranyloxy)-estra-1,3,5(10)-trien-16-one (IIa), crystallization from methanol gives 0.8 part of 3-methoxy-17β-(2'-tetrahydropyranyloxy)-estra-1,3,5(10)-trien-16β-ol (IIIa) of m.p. 130°—130° C. and $[\alpha]_D = 121°$ (chloroform).

EXAMPLE 9

3-Benzyloxy-17β-(2'-tetrahydropyranyloxy)-estra-1,3,5(10)-trien-16α-ol (IIIe)

Using a process identical to that described in Example 6 and starting from 3-benzyloxy-17β-(2'-tetrahydropyranyloxy)-estra-1,3,5(10)-trien-16-one (IIb), 3-benzyloxy-17β-(2'-tetrahydropyranyloxy)-estra-1,3,5(10)-trien-16α-ol (IIIe) is obtained.

EXAMPLE 10

3-Methoxy-17β-(2'-tetrahydropyranyloxy)-estra-1,3,5(10)-trien-16αol (IIId)

Using a process identical with that described in Example 6 and starting from 3-methoxy-17β-(2'-tetrahydropyranyloxy)-estra-1,3,5(10)-trien-16-one (IIa), 3-methoxy-17β-(2'tetrahydropyranyloxy)-estra-1,3,5(10)-trien-16α-ol (IIId) is obtained.

EXAMPLE 11

17β-(2'-tetrahydropyranyloxy)-estra-1,3,5(10)-trien-3,16β-diol (IIIg)

Using a process identical with that described under Example 3 and starting from 3 parts of 3-benzyloxy-17β-(2'-tetrahydropyranyloxy)-estra-1,3,5(10)-trien-16β-ol (IIb), crystallisation from ethyl ether gives 1.4 parts of 17β-(2'-tetrahydropyranyloxy)-estra-1,3,5(10)-trien-3,16β-diol (IIIg) of m.p. 173° C and $[\alpha]_D = +90°$ (chloroform).

The same compound is also obtained by reduction with NaBH₄ starting from IIc.

The 17β-(2'-tetrahydropyranyloxy)-estra-1,3,5(10)-trien-3,16β-diol thus obtained is a mixture of the two diastereoisomers R and S, as stated above. This mixture when subjected to fractional crystallization from methanol gave the pure form 17β-(2'-R-tetrahydropyranyloxy)-estra-1,3,5(10)-trien-3,16β-diol, m.p. 176° C $[\alpha]_D$ 115° (CHCl₃), and 17β(2'-S-tetrahydropyranyloxy)-estra-1,3,5(10)-trien-3,16β-diol, m.p. 184° C $[\alpha]_D$ +15° (CHCl₃).

EXAMPLE 12

17β-(2'-tetrahydropyranyloxy)-estra-1,3,5(10)-trien-3,16α-diol (IIIh)

Using the process identical with that described in Example 3 and starting from 3 parts of 3-benzyloxy-17β-(2'-tetrahydropyranyloxy)-estra-1,3,5(10)-trien-16α-ol (IIIc), crystallization from ethyl ether gives 0.8 part of 17β-(2'-tetrahydropyranyloxy)-estra-1,3,5(10)-triene-3,16α-diol (IIIh) of m.p. 220°–22° C. (dec.) and $[\alpha]_D = +58.5°$ (chloroform).

The same compound is also obtained by reduction of IIc with sodium in alcohol.

EXAMPLE 13

3-Benzyloxy-16β,17β-bis-(2'-tetrahydropyranyloxy)-estra-1,3,5(10)-triene IVb)

0.65 Part of 2,3-dihydropyran and 0.025 part of p-toluenesulphonic acid dissolved in 90 parts of anhydrous benzene are added to a solution of 0.7 part of 3-benzyloxy-17β-(2'-tetrahydropyranyloxy)-estra-1,3,5(10)-trien-16β-ol (IIIb) in 130 parts of anhydrous benzene. The reaction mixture is left overnight at room temperature, then washed with three portions of a 10% aqueous NaHCO₃ solution, and then with water until neutral. After drying, the organic phase is concentrated under vacuum to dryness. The uncrystallizable oily residue is chromatographed over a Al₂O₃ column (activity II according to Brockmann), eluting with a mixture of petroleum ether (b.p. 40°–70° C.) and ethyl ether. When the useful fractions are crystallized from the same mixture, they give 0.5 part of 3-benzyloxy-16β,17β-bis-(2'-tetrahydropyranyloxy)-estra-1,3,5(10)-triene (IVb), m.p. 65°–67° C. and $[\alpha]_D = +55.5°$ (chloroform).

EXAMPLE 14

3-Methoxy-16β,17β-bis-(2'-tetrahydropyranyloxy)-estra-1,3,5(10)-triene (1Va)

0.6 Part of 2,3-dihydropyran and 0.02 part of p-toluenesulphnoic acid dissolved in 90 parts of anhydrous benzene are added to a solution of 0.5 part of 3-methoxy-17β-(2'-tetrahydropyranyloxy)-estra-1,3,5(10)-trien-16β-ol (IIIa) in 120 parts of anhydrous benzene. The reaction mixture is left overnight at room temperature, then washed with three portions of a 10% aqueous solution of NaHCO₃, and then with water until neutral. The uncrystallizable oily residue is chromatographed over an Al₂O₃ column (acitivty II according to Brockmann), eluting with a mixture of petroleum ether (b.p. 40°–70° C.) and ethyl ether. The useful fractions give 0.4 part of 3-methoxy-16β,17β-bis-(2'-tetrahydropyranyloxy)-1,3,5(10)-triene (1Va) in the form of an uncrysta'lizable oil of $[\alpha]_D = +51.6°$ (chloroform).

EXAMPLE 15

16β,17β-Bis-(2'-tetrahydropyranyloxy)-estra-1,3,5(10)-trien-3-ol (1Vg)

Using a process analogous to that described in Example 3, but employing 90 parts of ethanol and 0.6 part of carbon containing 5% palladium, and starting from 0.6 part of 3-benzyloxy-16β,17β-bis-(2'-tetrahydropyranyloxy)estra-1,3,5(10)-triene (IVb), crystallization from ether-hexane gives 0.3 part of 16β,17β-bis-(2'-tetrahydropyranyloxy)-estra-1,3,5(10)-trien-3-ol (IVg), m.p. 107°–109° C. and $[\alpha]_D = +71°$ (chloroform).

EXAMPLE 16

3,16β,17β-tris-(2'-tetrahydropyranyloxy)-estra-1,3,5(10)-triene (IVc)

a. Using a process identical with that described under Example 4 and starting from 0.7 part of 16β,17β-bis-(2'-tetrahydropyranyloxy)-estra-1,3,5(10)-trien-3-ol (IVg), purification on a chromatographic column gives 0.5 part of 3,16β,17β-tris-(2'-tetrahydropyranyloxy)-estra-1,3,5(10)-triene (IVc) in the form of an uncrystallizable oil of $[\alpha]_D = +58.5°$.

b. The same product can also be obtained by etherification with 2,3-dihydropyran of the free alcoholic functions of 16β-epiestriol (Va), the 3,17-bis-pyranylether (IIIc), or the 17-monopyranylether (IIIg).

EXAMPLE 17

Compounds (IVe), (IVh) and (IVf)

Using the process identical to that described under Example 13 and starting from 3-benzyloxy-17β-(2'-tetrahydropyranyloxy)-estra-1,3,5(10)-trien-16α-ol (IIIe), 3-benzyloxy-16α,17β-bis-(2'-tetrahydropyranyloxy)-estra-1,3,5(10)-triene (IVe) is obtained.

This latter compound when treated in a manner identical with that described under Example 15 gives 16α,17β-bis-(2'-tetrahydropyranyloxy)-estra-1,3,5(10)-trien-3-ol (IVh), m.p. 140°–142° C. and $[\alpha]_D = 0$.

This latter compound when treated in a manner identical to that described in Example 4 gives 3,16α,17β-tris-(2'-tetrahydropyranyloxy)-estra-1,3,5(10)-triene (IVf), m.p. 149°–151° C. and $[\alpha]_D = 26.5°$ (chloroform).

The same product can also be obtained by etherification with 2,3-dihydropyran of the free alcoholic functions of estriol (Vb), the 3,17-bis-pyranylether (IIIf), or the 17-monopyranylether (IIIh).

EXAMPLE 18

3-Methoxy-16α,17β-bis-(2'-tetrahydropyranyloxy)-estra 1,3,5(10) -triene (IVd)

Using a process identical with that described in Example 14 and starting from 3-methoxy-17β-(2'-tetrahydropyranyloxy)-estra-1,3,5(10)-trien-16α-ol (IIId), 3-methoxy-16α,17β-bis-(2'-tetrahydropyranyloxy)-estra-1,3,5(10)-triene (IVd) is obtained, m.p. 127°–129° C. and $[\alpha]_D = 9,6°$ (chloroform).

EXAMPLE 19

Compounds (Vc) and (Vd)

Using a process identical to that described in Examples 5 and 6 and starting from 3-benzyloxy-estra-1,3,5(10)-trien-17β-ol-16-one (Ib), 3-benzyloxy-estra-1,3,5(10)-trien-16β,17β-diol (Vc) and the corresponding isomer 16β,17β-diol (Vd) are obtained respectively.

What is claimed is:

1. Process for preparing a compound of the formula

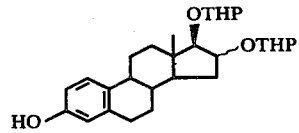

which comprises debenzylating by catalytic hydrogenation the corresponding 3-benzyloxy-16α- or 16β-, 17β-bis-(2'-tetrahydropyranyloxy) compound in an organic solvent.

2. Process according to claim 1 in which the hydrogenation is effected in ethanol, alone or with dioxane, tetrahydrofuran or ethyl acetate, in the presence of 2.5 to 10% Pd on carbon.

3. A compound comprising of 3-benzyloxy-17β-(2'-tetrahydropyranyloxy)-estra-1,3,5(10)-trien-16-one.

4. A compound comprising of 3-methoxy-17β-(2'-tetrahydropyranyloxy)-estra-1,3,5(10)-trien-16-one.

5. A compound comprising of 17β-(2'-tetrahydropyranyloxy)-estra-1,3,5(10)-trien-16-one.

6. A compound comprising of 3,17β-bis-(2'-tetrahydropyranoloxy)-estra-1,3,5(10-trien-16-one.

7. A compound comprising of 3-benzyloxy-17β-(2'-tetrahydropyranyloxy)-estra-1,3,5 (10)-trien-16β-ol.

8. A compound comprising of 3-methoxy-17β-(2'-tetrahydropyranyloxy)-estra-1,3,5 (10)-trien-16β-ol.

9. A compound comprising of 3-benzyloxy-17β-(2'-tetrahydropyranyloxy)-estra-1,3,5 (10)-trien-16α-ol.

10. A compound comprising of 3-methoxy-17β-(2'-tetrahydropyranyloxy)-estra-1,3,5 (10)-trien-16α-ol.

11. A compound comprising of 3-benzyloxy-16β,17β-bis-(2'-tetrahydropyranyloxy)-estra-1,3,5(10)-triene.

12. A compound comprising of 3-methoxy-16β,17β-bis-(2'-tetrahydropyranyloxy)-estra-1,3,5(10)-triene.

13. A compound comprising of 16β,17β-bis-(2'-tetrahydropyranyloxy)-estra-1,3,5(10)-trien-3-ol.

14. A compound comprising of 3-methoxy-16α,17β-bis-(2'-tetrahydropyranyloxy)-estra-1,3,5(10)-triene.

* * * * *

UNITED STATES PATENT AND TRADEMARK OFFICE
CERTIFICATE OF CORRECTION

PATENT NO. : 4,048,159
DATED : September 13, 1977
INVENTOR(S) : Pietro De Ruggieri et al It is certified that error appears in the above-identified patent and that said Letters Patent are hereby corrected as shown below:

Column 9, line 14 should read:

--dropyranyloxy)-estra-1,3,5(10)-trien-3-ol-16-one--.

Signed and Sealed this

Twenty-first Day of March 1978

[SEAL]

Attest:

RUTH C. MASON
Attesting Officer

LUTRELLE F. PARKER
Acting Commissioner of Patents and Trademarks